United States Patent
Wu (10) Patent No.: US 7,172,424 B2
(45) Date of Patent: Feb. 6, 2007

(54) METHOD OF MOUNTING REMOVABLE RESTORATION TOOTH BY USING A STANDARDIZED SET OF INNER CROWN UNITS, OUTER CROWN UNITS, AND DEVICE UNITS FOR CONFORMING ABUTMENT

(76) Inventor: Wen Yuen Wu, Dashuen 1st Rd., Kaohsiung (TW) 813

( * ) Notice: Subject to any disclaimer, the term of this patent is extended or adjusted under 35 U.S.C. 154(b) by 338 days.

(21) Appl. No.: 10/929,498

(22) Filed: Aug. 31, 2004

(65) Prior Publication Data
US 2005/0074725 A1    Apr. 7, 2005

(30) Foreign Application Priority Data
Oct. 2, 2003    (TW) ............... 92127268 A (51) Int. Cl.
*A61C 5/10*    (2006.01)
*A61C 13/08*    (2006.01)

(52) U.S. Cl. .............. 433/223; 433/218; 264/19
(58) Field of Classification Search ............. 433/223, 433/208, 218; 264/19, 20
See application file for complete search history.

(56) References Cited
U.S. PATENT DOCUMENTS

| | | | | |
|---|---|---|---|---|
| 3,052,982 A | * | 9/1962 | Weinstein et al. | 433/206 |
| 3,375,582 A | * | 4/1968 | Myerson | 433/223 |
| 3,457,644 A | * | 7/1969 | Susman et al. | 433/213 |
| 4,332,564 A | * | 6/1982 | Lord | 433/218 |
| 4,398,887 A | * | 8/1983 | Balde et al. | 433/218 |
| 4,775,319 A | * | 10/1988 | Knapp | 433/40 |
| 4,952,151 A | * | 8/1990 | Metcalfe | 433/223 |
| 5,346,397 A | * | 9/1994 | Braiman | 433/223 |
| 5,487,663 A | * | 1/1996 | Wilson | 433/218 |
| 5,827,063 A | * | 10/1998 | Greenstein | 433/213 |
| 6,869,552 B2 | * | 3/2005 | Glidewell | 264/16 |

* cited by examiner

*Primary Examiner*—John J Wilson
(74) *Attorney, Agent, or Firm*—Bacon & Thomas, PLLC (57) ABSTRACT

A method is designed to mount a removable restoration tooth on a natural tooth to be restored. The method involves the use of the standardized plastic inner crowns corresponding to the permanent teeth of a human, the standardized metal outer crowns corresponding to the plastic inner crowns, and the standardized abutment conformation devices corresponding to the plastic inner crowns. One of the devices is used as a reference in forming an abutment on the natural tooth. An abutment matrix is made to facilitate the dressing of the plastic inner crown, so as to make a metal inner crown according to the dressed plastic inner crown. The metal inner crown is mounted on the abutment. A metal outer crown corresponding to the plastic inner crown is fitted with the restoration tooth, which is mounted on the natural tooth such that the metal outer crown is fitted over the metal inner crown.

5 Claims, 12 Drawing Sheets

METHOD OF MOUNTING REMOVABLE RESTORATION TOOTH BY USING A STANDARDIZED SET OF INNER CROWN UNITS, OUTER CROWN UNITS, AND DEVICE UNITS FOR CONFORMING ABUTMENT

FIELD OF THE INVENTION

The present invention relates generally to a dental method of mounting a detachable restoration tooth on an abutment tooth, and more particularly to a method of mounting a detachable restoration tooth by using a modular set of inner crown units, outer crown units, and device units which are used for abutment conformation.

BACKGROUND OF THE PRESENT INVENTION

As illustrated in FIGS. 1–4, a conventional method of mounting a removable restoration tooth "T" involves a first step in which an abutment 11 is formed on a tooth 10 to be restored. Thereafter, a matrix of the abutment 11 is made. On the basis of the matrix of the abutment 11, a metal inner crown 20 of a hollow construction is made. A matrix of the inner crown 20 is made for preparation of an outer crown 30. The inner crown 20 is fitted fixedly over the abutment 11 such that an inner wall 21 of the inner crown 20 is joined with the abutment 11 in conjunction with a cement "C". Finally, the outer crown 30 of the restoration tooth "T" is removable fitted over an outer wall 22 of the inner crown 20. It must be noted here that the association of the outer wall 22 of the inner crown 20 and the inner wall 31 of the outer crown 30 of the restoration tooth "T" takes the form of interference fit.

The efficiency of the conventional method described above is dependent on the quality of dental works done by a dentist and a dental technician. For example, the formation of the abutment 11 and the making of the matrix of the abutment 11 are done by the dentist. The inner crown 20 is made by the dental technician on the basis of the matrix of the abutment 11. The outer crown 30 of the restoration tooth "T" is also made by the dental technician. It is therefore readily apparent that a work done by the dentist is a complement to the dental technician and vice versa. In addition, the making of the inner crown 20 is a time-consuming chore on the part of the dental technician in view of the fact that the inclination of the outer wall 22 of the inner crown 20 is crucial to a successful interference fit between the outer wall 22 of the inner crown 20 and the inner wall 31 of the outer crown 30 of the restoration tooth "T".

Figure 1:
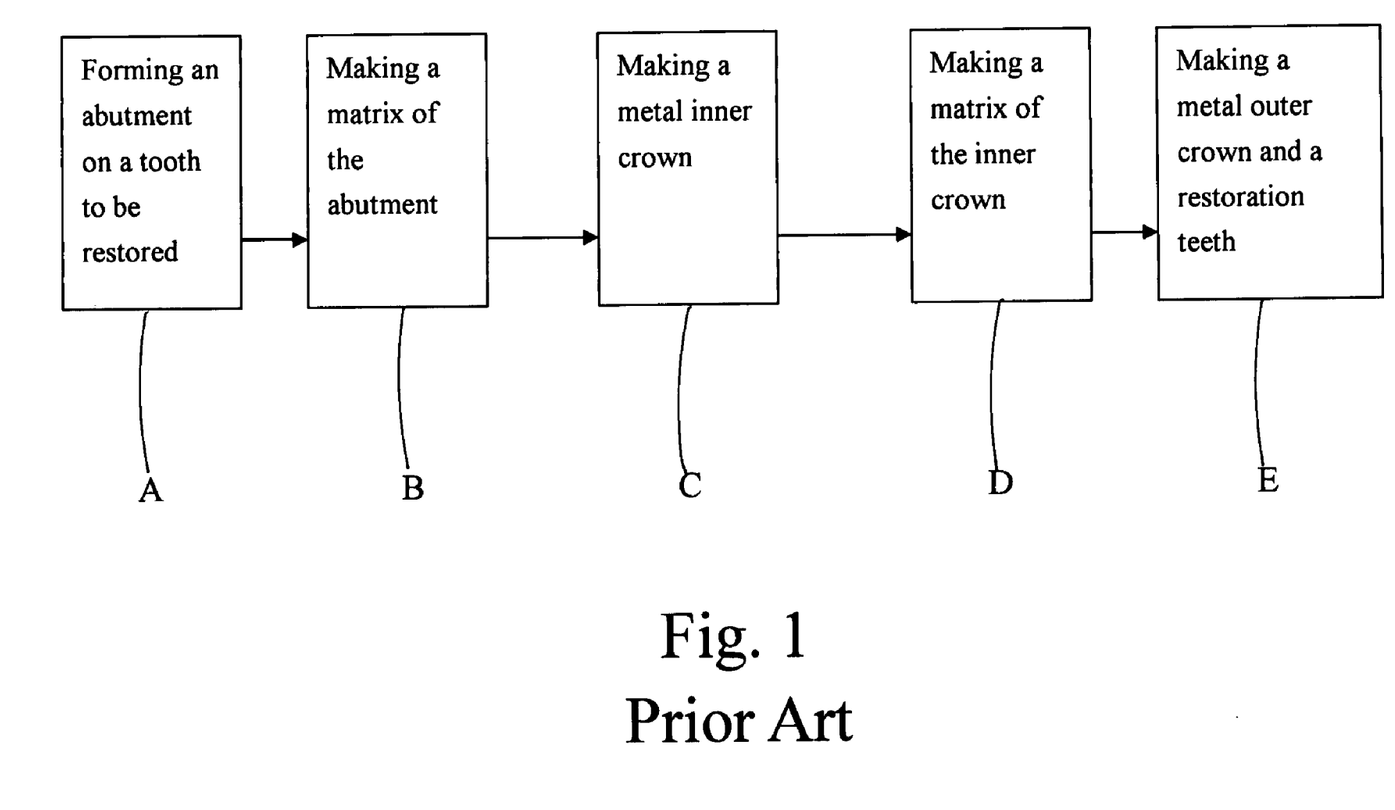
FIG. 1 shows a process flow diagram of a removable restoration tooth of the prior art.
Figure 2:
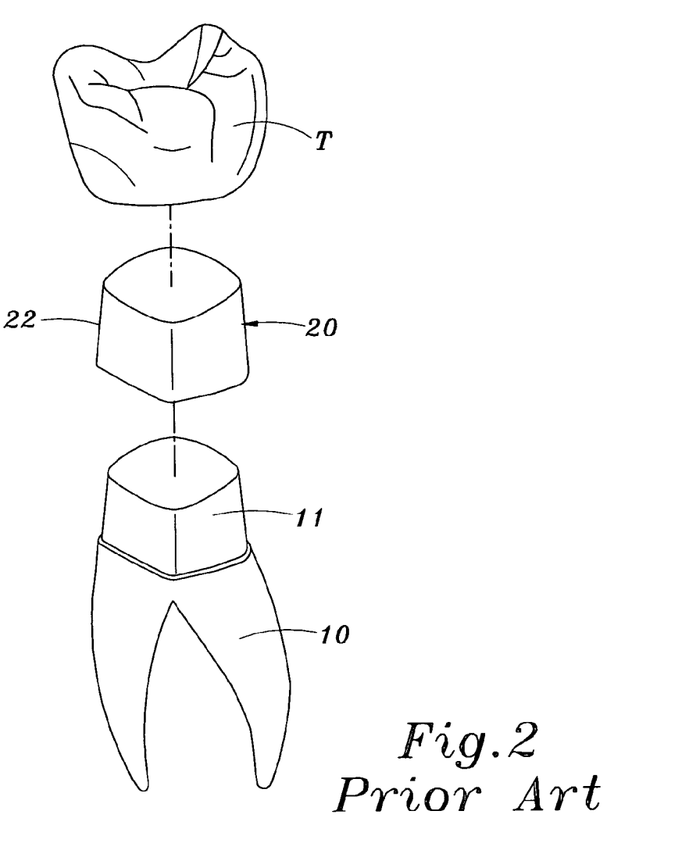
FIG. 2 shows an exploded view of the removable restoration tooth of the prior art.
Figure 3:
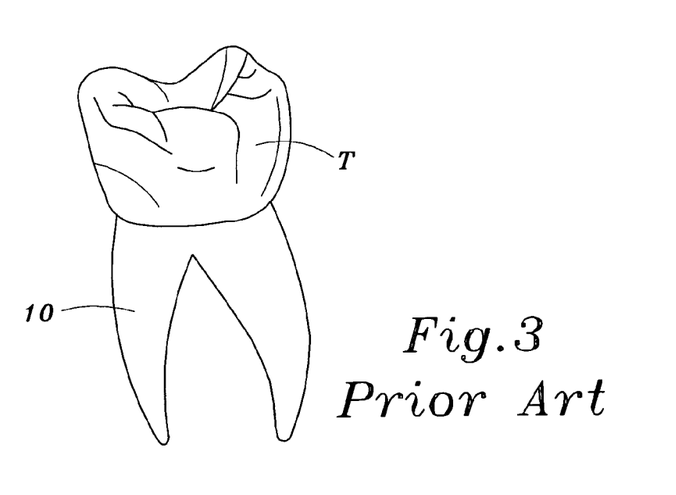
FIG. 3 shows a perspective view of the removable restoration tooth of the prior art in combination.
Figure 4:
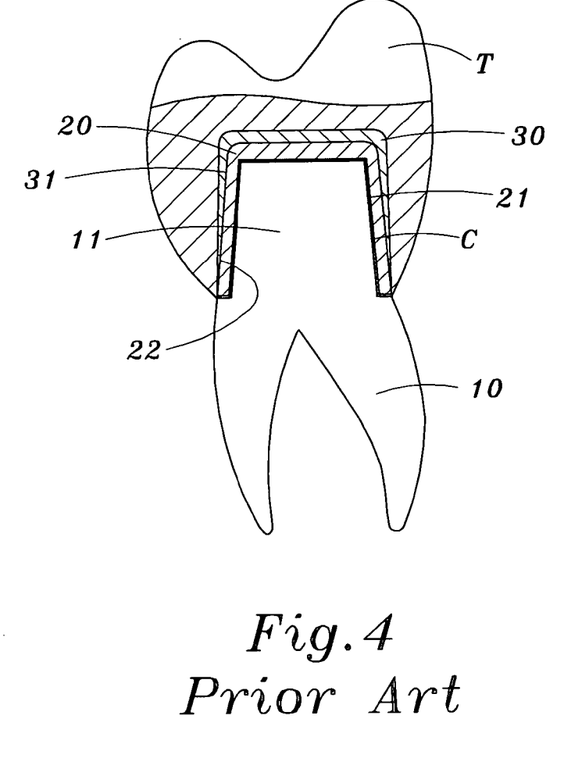
FIG. 4 shows a longitudinal sectional view of the removable restoration tooth of the prior art in combination.
Figure 5:
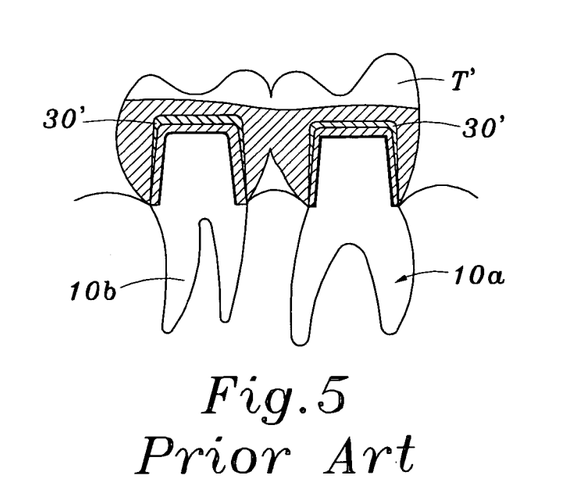
FIG. 5 shows a longitudinal sectional view of two prior art removable restoration teeth mounted side by side.
Figure 6:
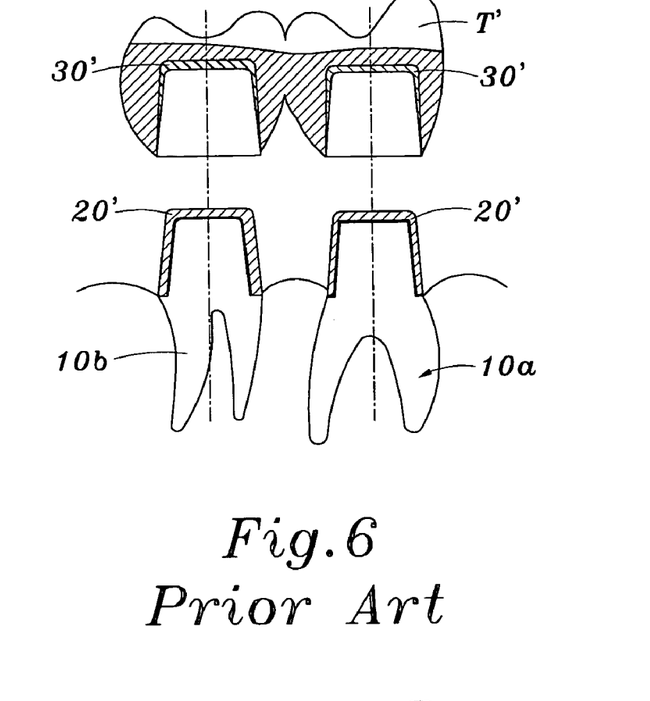
FIG. 6 shows an exploded sectional view of the two prior art removable restoration teeth as shown in FIG. 5.
Figure 7:
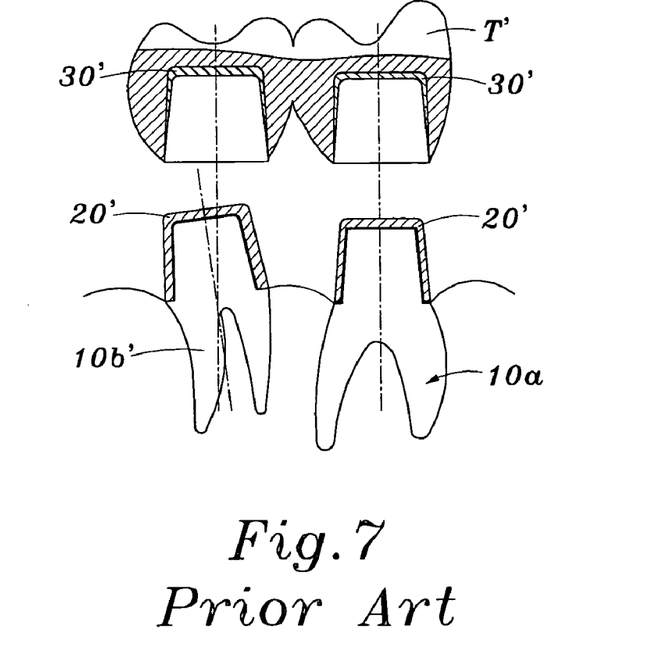
FIG. 7 shows another exploded sectional view of the two prior art removable restoration teeth as shown in FIG. 5.

The conventional method described above has another limitation. As illustrated in FIGS. 5–7, there are two natural teeth 10a and 10b which are to be restored by a restoration tooth "T'" having two outer crowns 30'. The restoration tooth "T'" is joined with the two natural teeth 10a and 10b such that the two outer crowns 30' are respectively fitted over the abutments 20' of the two natural teeth 10a and 10b under the circumstances that the center lines of the two abutments 20' are parallel to each other. In the event that the two abutments 20' are not made correctly by a dentist, it is very likely that the center lines of the two abutments 20' are not parallel to each other, as illustrated in FIG. 7. As a result, the two outer crowns 30' of the restoration tooth "T'" are not properly fitted over the two abutments 20'.

SUMMARY OF THE PRESENT INVENTION

The primary objective of the present invention is to provide a novel method of mounting a removable restoration tooth on a natural tooth to be restored. The method of the present invention is free of the deficiencies of the prior art method described above.

The method of the present invention employs a standardized set of 32 inner crown units, 32 outer crown units, and 32 device units for conforming the abutments. With the help of device units, the formation of abutment on a natural tooth to be restored is done efficiently and precisely. In addition, the device units are provided with a rod by means of which a dentist can easily determine if the center lines of two adjoining abutments are parallel to each other.

The standardized sets of the inner crown units and the outer crown units serve to streamline the process of making the metal inner crowns.

The features and the advantages of the present invention will be more readily understood upon a thoughtful deliberation of the following detailed description of a preferred embodiment of the present invention with reference to the accompanying drawings.

DETAILED DESCRIPTION OF THE PREFERRED EMBODIMENT

Figure 8:
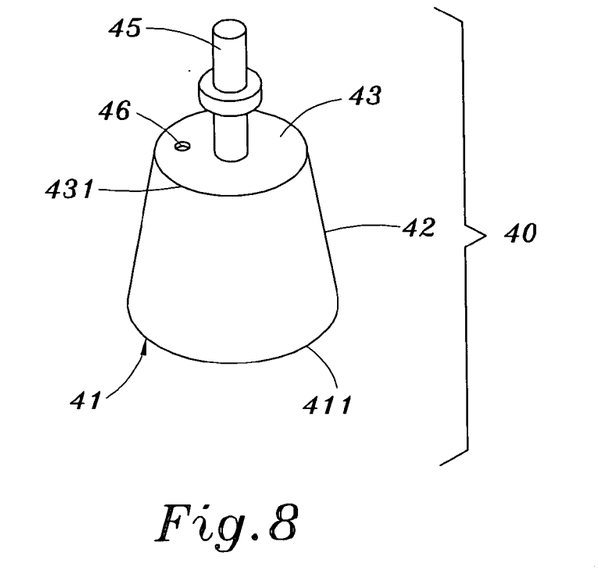
FIG. 8 shows a perspective view of an inner crown of the present invention.
Figure 9:
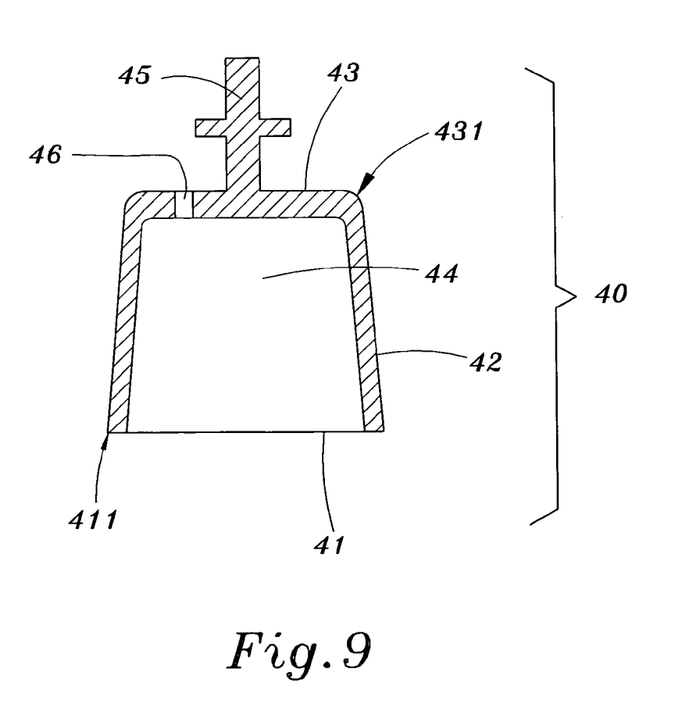
FIG. 9 shows a sectional schematic view of the inner crown of the present invention.

As shown in FIGS. 8–9, the present invention comprises a standardized set of plastic inner crowns 40, which are corresponding in shape and size to the 16 upper teeth and 16 lower teeth of the permanent teeth of a human. The plastic inner crowns 40 are integrally made by injection molding. In the event that any one of these 32 permanent teeth is to be restored due to decay or deformation, one of the 32 plastic inner crowns 40 is selected by a dentist for use in the treatment of the diseased or deformed tooth. The selected plastic inner crown 40 is corresponding in shape and size to the diseased or deformed tooth to be restored.

The plastic inner crowns 40 are of a conical construction, each of the plastic inner crowns 40 has a bottom 41 with a fringe 411, a conical body 42 with a hollow interior 44, and a top 43 with a fringe 431. The conical body 42 is located between the bottom 41 and the top 43, with the hollow interior 44 extending from the bottom 41 toward the top 43. The hollow interior 44 is dimensioned to fit with the abutment of a natural abutment tooth. The top 43 is provided in the center with a cruciform engagement portion 45 and is further provided with a ventilation hole 46 in communication with the hollow interior 44, as shown in FIG. 9. The conical body 42 has an outer wall with an inclination.

Figure 10:
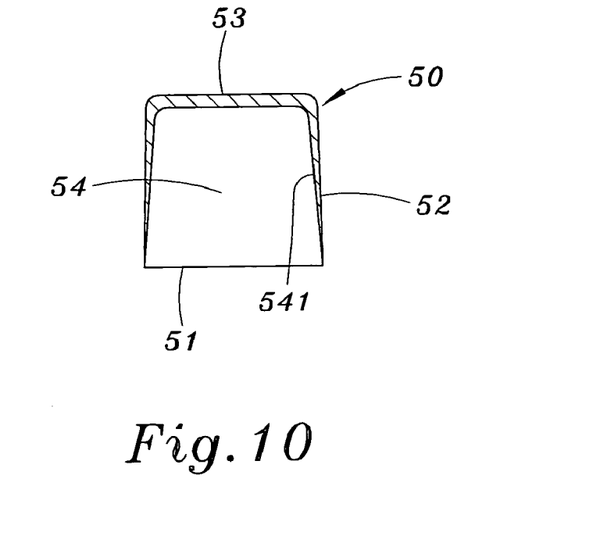
FIG. 10 shows a sectional schematic view of an outer crown of the present invention.

As shown in FIG. 10, the present invention comprises a standardized set of metal outer crowns 50 of 32 different specifications in conformity with the 32 plastic inner crowns 40. The metal outer crowns 50 have a bottom 51, an outer wall 52, a top 53, and a hollow interior 54 extending from the bottom 51 toward the top 53. The hollow interior 54 has an upright inner wall 541 corresponding in inclination to the outer wall of the conical body 42 of the plastic inner crowns 40. The outer wall 52 is located between the fringe of the bottom 51 and the fringe of the top 53.

Figure 11:
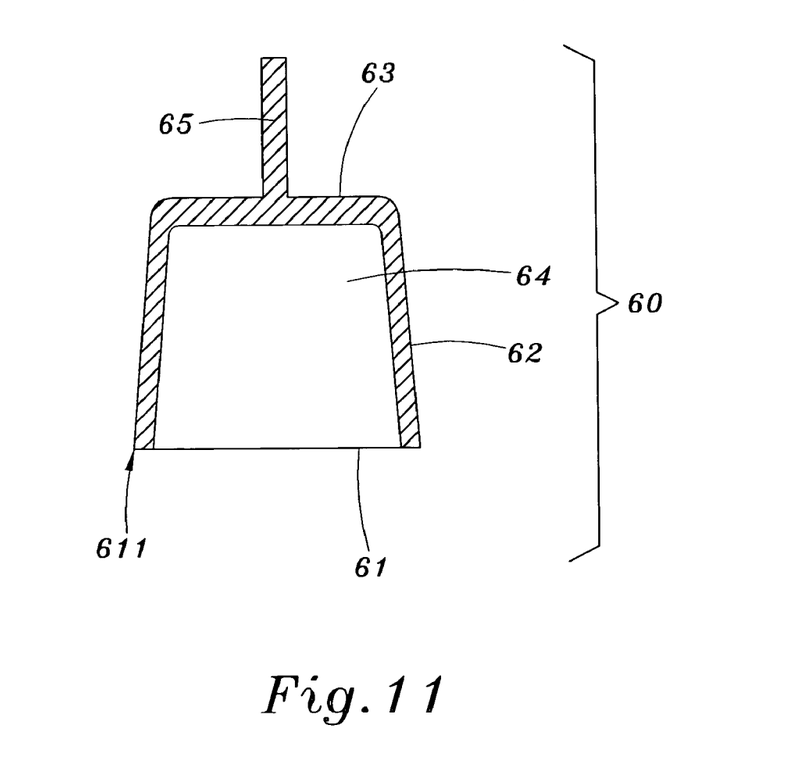
FIG. 11 shows a sectional schematic view of an abutment conformation device of the present invention.

As shown in FIG. 11, the present invention comprises a standardized set of 32 abutment conformation devices 60.

In terms of specifications, these 32 abutment conformation devices 60 are in conformity with the plastic inner crowns 40. The abutment conformation devices 60 are used as references to form abutment of a natural abutment tooth. The devices 60 have a bottom 61, a top 63, an outer wall 62 located between a fringe 611 of the bottom 61 and a fringe of the top 63, and a hollow interior 64 extending from the bottom 61 toward the top 63. The hollow interior 64 has a standardized dimension and serves as a guide to form the abutment of the natural abutment tooth. The top 63 is provided in the center with a rod 65 extending uprightly therefrom.

Figure 12:
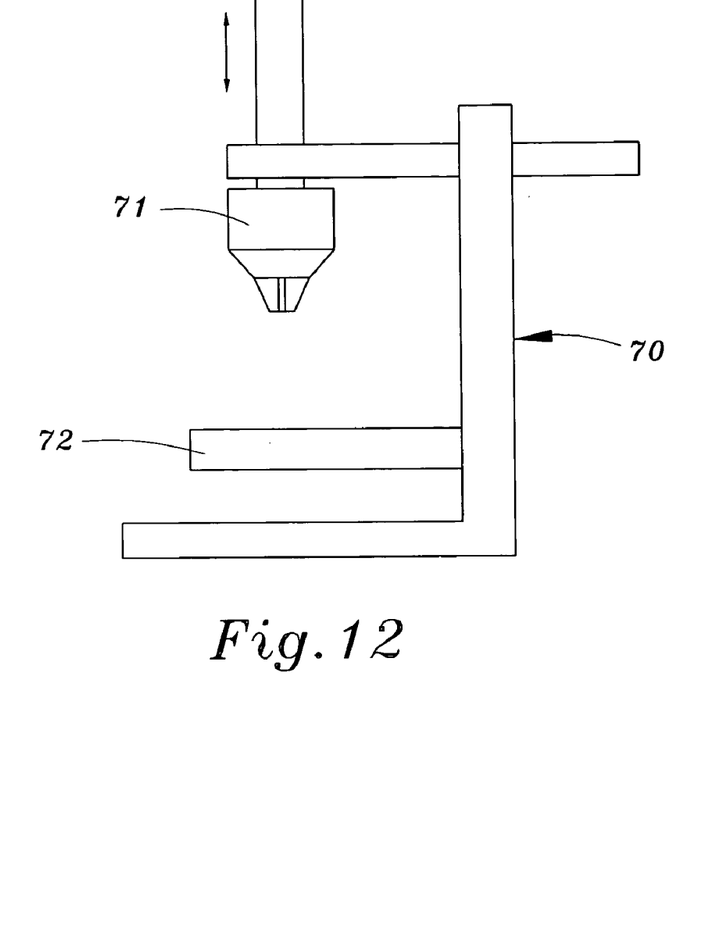
FIG. 12 shows a schematic view of a holding device used by the dental technician.
Figure 13:
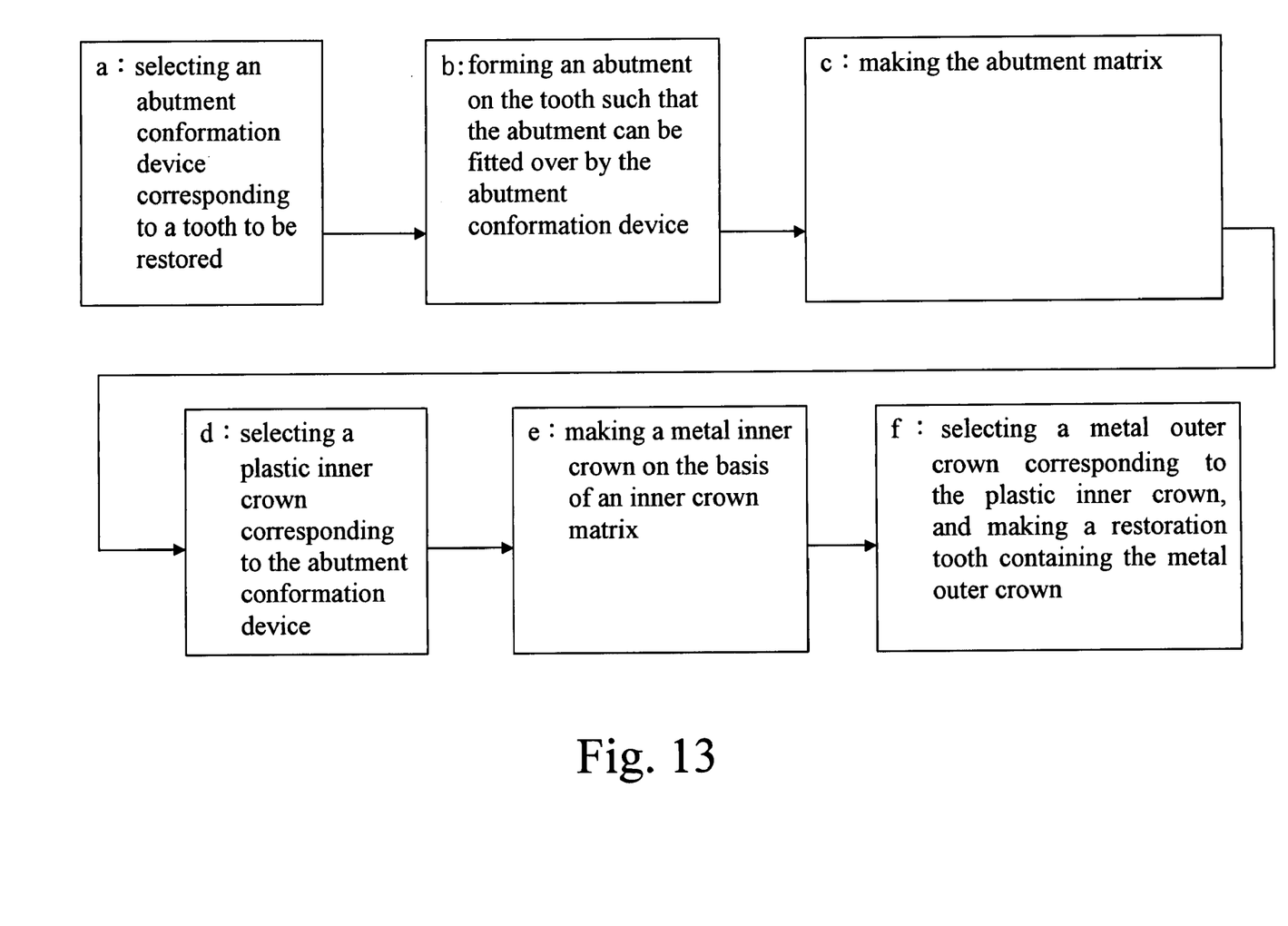
FIG. 13 shows a flow chart of the present invention.
Figure 14:
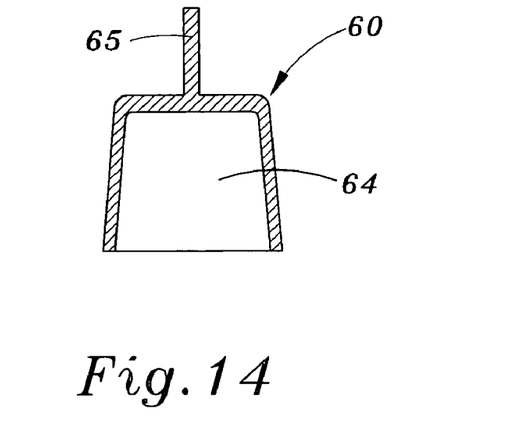
FIG. 14 shows a sectional schematic view of a selected abutment conformation device of the present invention.

As shown in FIG. 12, a holding device 70 is commonly used by the dental technician to hold a plastic inner crown and an abutment matrix. The holding device 70 comprises a chuck 71 capable of an up-and-down movement, and a platform 72 capable of a horizontal displacement. The chuck 71 is used to hold the engagement portion of the plastic inner crowns 40. The platform 72 is used to hold the abutment matrix which is made by the dentist.

As shown in FIGS. 13–20, a method of the present invention is used to mount a removable restoration tooth on a natural abutment tooth which is a diseased or deformed tooth and is to be restored by the removable restoration tooth.

Figure 15:
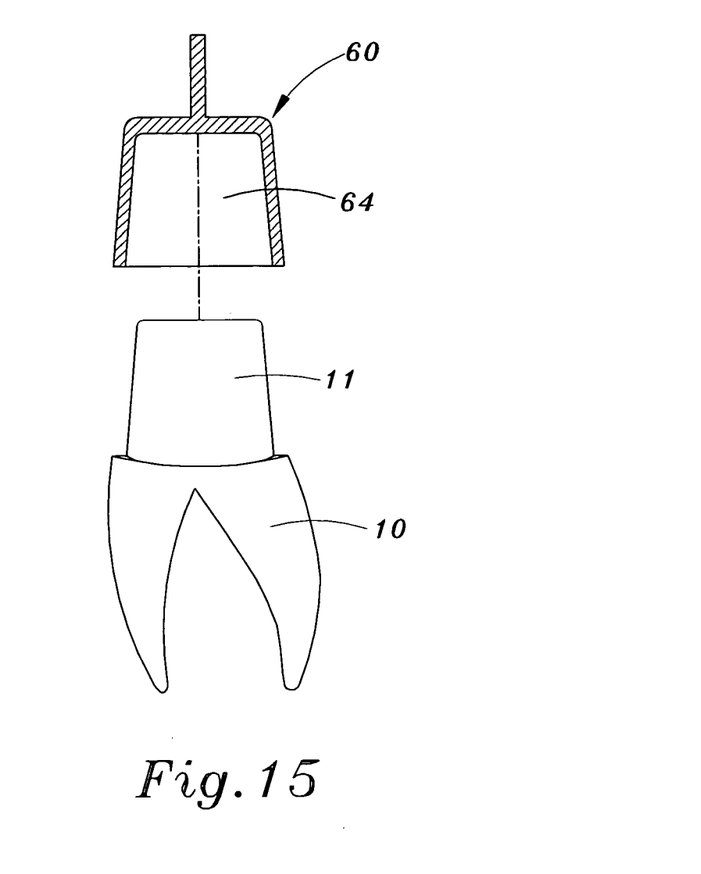
FIG. 15 shows a schematic view of an abutment tooth in relation to the selected abutment conformation device of the present invention.
Figure 16:
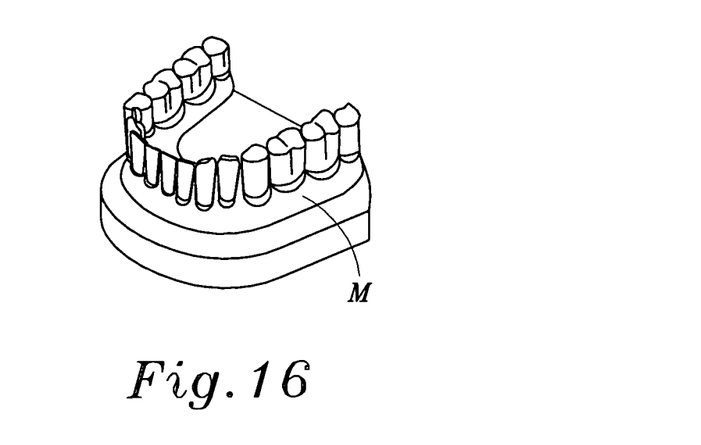
FIG. 16 shows a schematic view of the making of an abutment matrix of the present invention.
Figure 17:
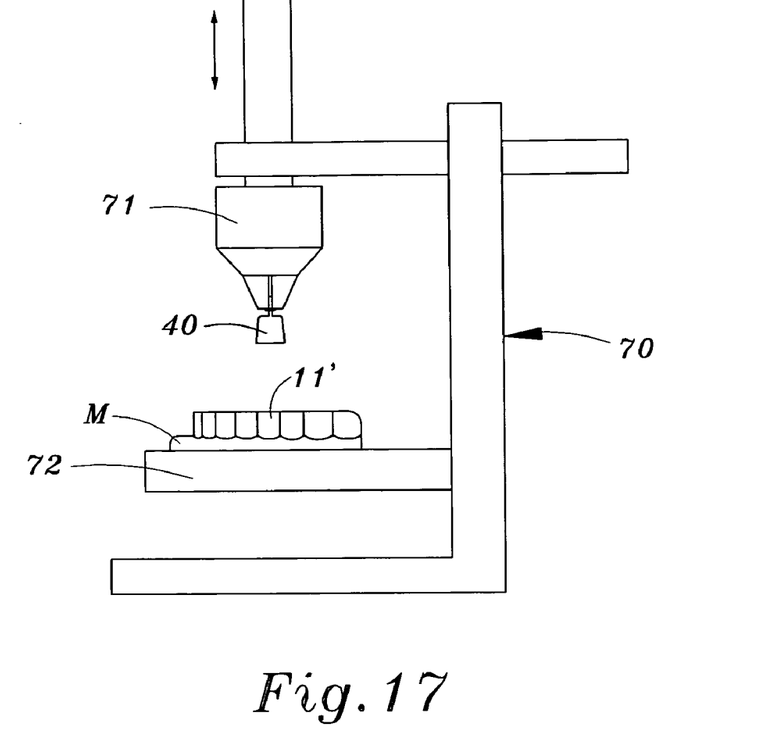
FIG. 17 is a schematic view showing that an engagement portion of the inner crown is held by a chuck of the holding device, and that the inner crown matrix is located on a plotform of the holding device.
Figure 18:
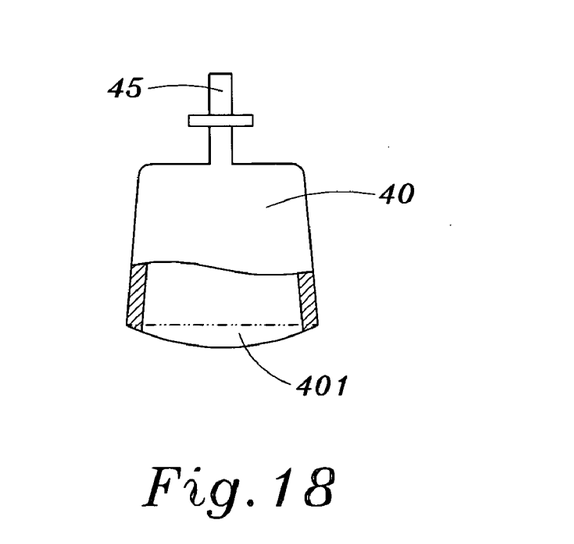
FIG. 18 shows a schematic view of the dressing of the metal inner crown of the present invention.
Figure 19:
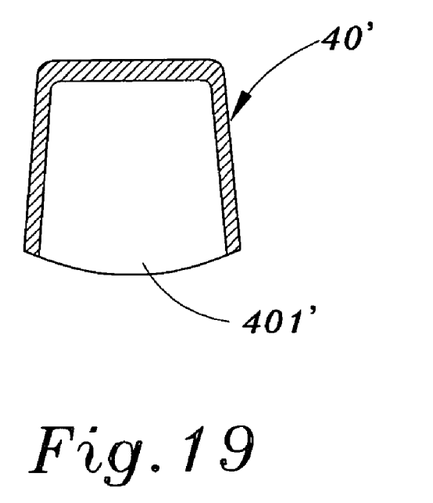
FIG. 19 shows a sectional schematic view of the metal inner crown of the present invention.
Figure 20:
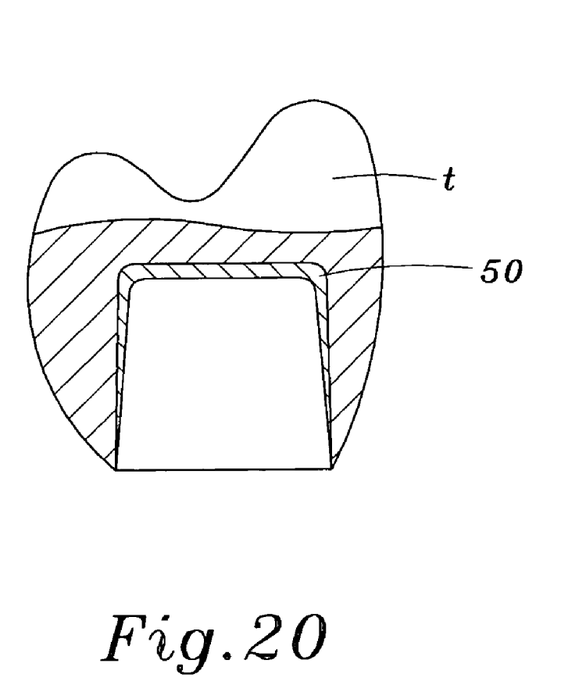
FIG. 20 shows a sectional schematic view of a restoration tooth of the present invention.
Figure 21:
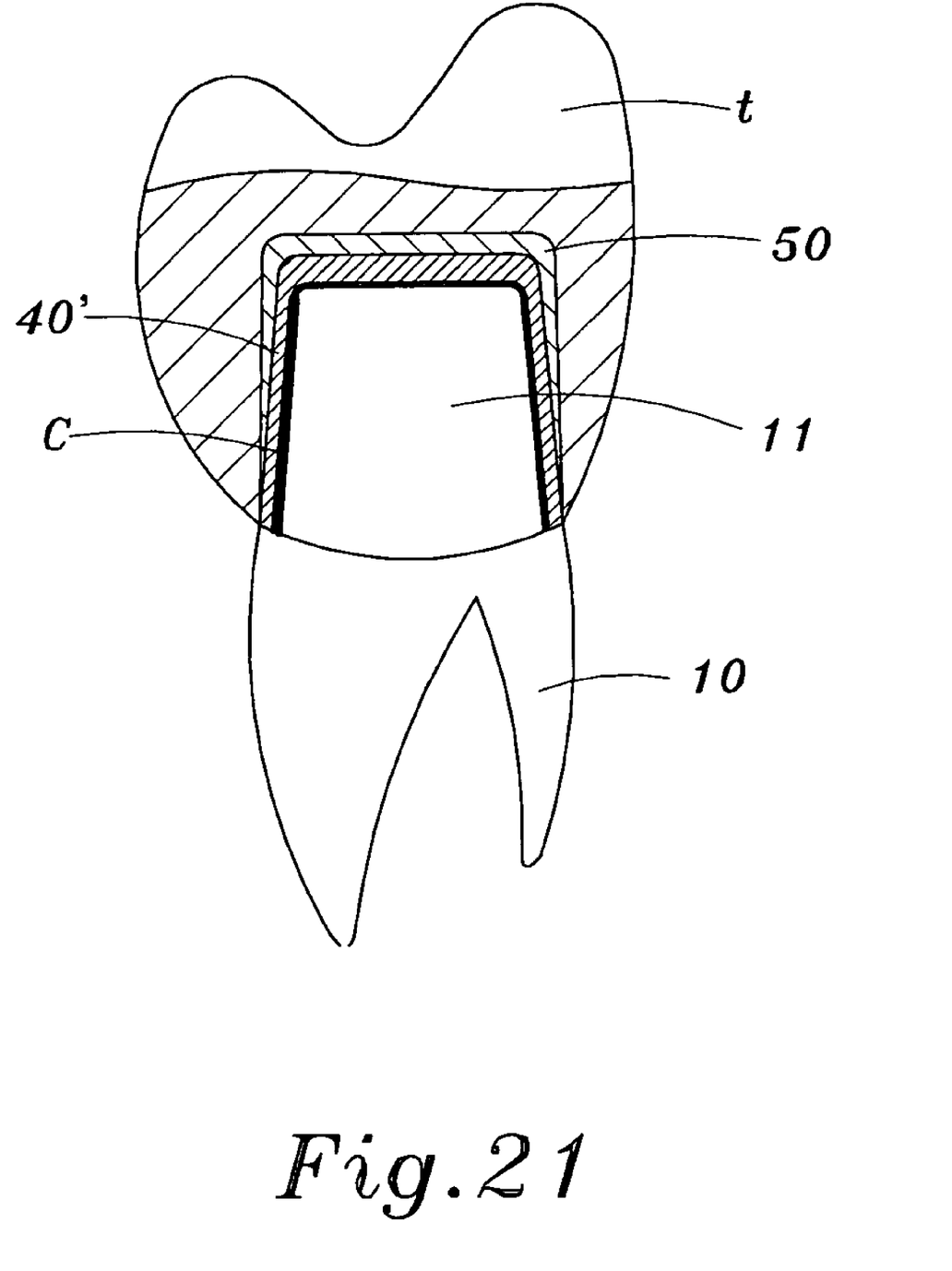
FIG. 21 shows a sectional schematic view of the restoration tooth of the present invention mounted on the abutment of a natural abutment tooth.

The method of the present invention comprises a first step in which a specific device 60 in conformity with a natural tooth 10 to be restored is selected by the dentist. An abutment 11 is formed on the natural tooth 10 such that the abutment 11 fits into the hollow interior 64 of that specific device 60, as illustrated in FIG. 15. A matrix "M" of the abutment 11 is made, as shown in FIG. 16. Thereafter, a plastic inner crown 40 corresponding in specifications to that specific device 60 is held by the holding device 70 such that the engagement proton 45 of the plastic inner crown 40 is held by the chuck 71 of the holding device 70. The matrix of the abutment 11 is located on the platform 72 of the holding device 70, as illustrated in FIG. 17. By moving the chuck 71 up and down, the plastic inner crown 40 is fitted with an abutment 11' of the abutment matrix "M". In accordance with the shape of the gum line of the matrix, the dressing of a line 401 of the plastic inner crown 40 is done, as illustrated in FIG. 18. Accordingly, a metal inner crown 40' is made in such a way that it has a line 401' in conformity with the gum line of the natural abutment tooth 10, as shown in FIG. 19. Finally, a metal outer crown 50 is selected such that its specifications match those of the plastic inner crown 40. The metal outer crown 50 is held in a restoration tooth "t", as shown in FIG. 20. The natwral abutment tooth 10 is restored by the restoration tooth "t" in such a manner that the metal outer crown 50 is removably fitted over the metal inner crown 40' which is in turn mounted fixedly on the abutment 11 of the natural abutment tooth 10 in conjunction with a cement "C", as shown in FIG. 21.

With the help of the standardized set of the device units 60, the formation of the abutment of a natural tooth to be restored is so streamlined as to enhance the efficiency of the dental treatment. The device units 60 are provided with a rod 65, by means of which a dentist can easily tell if the center lines of two adjoining abutments are parallel to each other. As a result, the quality of a dental work done by the dentist is greatly improved.

With the use of the standardized set of the plastic inner crown units 40 and the holding device 70, the efficiency and the precision of dressing a metal inner crown 40' are so enhanced that the problem of fitting the metal inner crown 40' with the gum line of a natural abutment tooth is substantially alleviated.

The standardized set of the metal outer crown units 50 are made in accordance with the standardized set of the plastic inner crown units 40. As a result, the method of the present invention eliminates the process of making an inner crown matrix, which is an indispensable step of the prior art method.

The embodiment of the present invention described above is merely illustrative. Accordingly, the present invention may be embodied in other specific forms without deviating from the spirit thereof. The present invention is therefore to be limited only by the scopes of the following claims.

What is claimed is:

1. A method of mounting a removable restoration tooth on a natural tooth to be restored, said method comprising the following steps of:
 (a) making 32 plastic inner crowns corresponding to 32 permanent teeth of a human, 32 metal outer crowns corresponding to the 32 plastic inner crowns, and 32 abutment conformation device units corresponding to the 32 plastic inner crowns;

(b) forming an abutment on the natural tooth such that the abutment fits into a hollow interior of one of the 32 abutment conformation device units corresponding to the natural tooth;
(c) making a matrix of the abutment;
(d) selecting a plastic inner crown from the 32 plastic inner crowns such that the plastic inner crown is corresponding to the natural tooth;
(e) holding the plastic inner crown with the chuck of a holding device and locating the abutment matrix on a platform of the holding device;
(f) fitting the plastic inner crown over the abutment matrix for dressing the plastic inner crown according to the gum line of the abutment matrix;
(g) making a metal inner crown according to the dressed plastic inner crown obtained in the stop (f);
(h) mounting fixedly the metal inner crown on the abutment of the natural tooth to be restored;
(i) selecting a metal outer crown from the 32 metal outer crowns referred to in the step (a) such that the metal outer crown is corresponding to the plastic inner crown, and that the metal outer crown is fitted into the removable restoration tooth; and
(j) mounting the restoration tooth on the natural tooth such that the metal outer crown is fitted over the metal inner crown which is fixedly mounted on the abutment of the natural tooth to be restored.

2. A method as recited in claim 1, wherein said each of the 32 plastic inner crowns has a conical body which is provided in a top thereof with an engagement portion, and in an interior thereof with a receiving space extending in the direction toward the top from a bottom thereof whereby the conical body has an outer wall of an inclination; wherein each of the 32 metal outer crowns has a top, an outer wall, a bottom, and a hollow interior extending from the bottom toward the top whereby the hollow interior has an inner wall corresponding in inclination to the outer wall of the conical body of the plastic inner crown; wherein said each of the 32 abutment conformation device units has a top; a bottom, an outer wall located between the top and the bottom, and a hollow interior extending from the bottom toward the top whereby the hollow interior has an inner wall corresponding in inclination to the outer wall of the conical body of the plastic inner crown.

3. A method as recited in claim 2, wherein said the top of the conical body of the 32 plastic inner crowns is provided with a ventilation hole in communication with the receiving space of the interior of the conical body.

4. A method as recited in claim 2, wherein said engagement portion of the conical body of the plastic inner crown is used to engage the chuck of the holding tool.

5. A method as recited in claim 2, wherein said top of the abutment conformation device units is provided with an upright, projection extending therefrom whereby the upright projection is intended to facilitate a dentist to observe the position of a center line of the abutment in the course of forming the abutment on the natural tooth to be restored.

* * * * *